United States Patent [19]

Bosch et al.

[11] Patent Number: 5,837,875
[45] Date of Patent: Nov. 17, 1998

[54] TRANSGENIC MOUSE CONTAINING AN IGF-1 TRANSGENE

[75] Inventors: Fatima Bosch; Alfons Valera, both of Bellaterra, Spain

[73] Assignee: The Autonomous University of Barcelona, Bellaterra, Spain

[21] Appl. No.: 578,245

[22] Filed: Dec. 26, 1995

Related U.S. Application Data

[60] Provisional application No. 60/004,260 Sep. 25, 1995.

[51] Int. Cl.$^6$ .............................. C12N 5/00; C12N 15/00; C12N 15/09
[52] U.S. Cl. ........................... 800/2; 435/172.3; 435/69.1; 435/69.4; 435/325; 435/320.1; 435/4; 424/9.21
[58] Field of Search .............................. 800/2; 435/172.3, 435/240.2, 320.1, 69.1, 69.4, 325; 536/23.1, 23.5; 935/23, 78, 79, 70, 71; 424/9.21

[56] References Cited

U.S. PATENT DOCUMENTS 5,529,920  6/1996  Cole et al. ............................ 435/240.2

OTHER PUBLICATIONS

Houdebine, Journal of Biotechnology, vol. 34, pp. 269–287, 1994.
Wall, Theriogenology, vol. 45, pp. 57–68, 1996.
Kappel et al., Current Opinion in Biotechnology, vol. 3, pp. 546–553, 1992.
Strojek & Wagner, Genetic Engineering: Principles and Methods, vol. 10, pp. 221–246, 1988.
Mathews et al., Endocrinology, vol. 123, pp. 2827–2833, 1988.
Melloul et al., Diabetologia, vol. 37, pp. S3–S10, Sep. 1994.
Sherwin et al., Hormone Research, vol. 41, pp. 97–102, 1994.
Bell et al., Nucleic Acids Research, vol. 14, pp. 7873–7882, 1986.
Dandoy–Dron et al., Nucleic Acids Research, vol. 19, pp. 4925–4930, 1991.
Landias et al., Journal of Immunology, vol. 137, p. 3002, 1986.
Bohme et al., "Transgenic Mice with I–A on Islet Cells Are Normoglycemic But Immunologically Intolerant", Science 244:1179–1183, 1989.
Efrat et al., "Glucagon Gene Regulatory Region Directs Oncoprotein Expression to Neurons and Pancreatic a Cells", Neuron 1:605–613, 1988.
Guler et al., "Effects of Recombinant Insulin–like growth factor I on Insulin Secretion and Renal Function in Normal Human Subjects", Medical Sciences 86:2868–2872, 1989.
Leahy et al., "Insulin–like Growth Factor–I at Physiological Concentrations Is a Potent Inhibitor of Insulin Secretion", Endocrinology 126:1593–1598, 1990.
Lee et al., "Demonstration that Polyol Accumulation is Responsible for Diabetic Cataract by the Use of Transgenic Mice . . . ", Proc. Natl. Acad. Sci. 92:2780–2784, 1995.
Maake et al., "Immunohistochemical Localization of Insulin–like Growth Factor 1 and 2 in the Endocrine Pancreas of Rat, Dog, and Man, . . . ", Cell Tissue Res 273:249–259, 1993.
Mathews et al., "Regulation of Insulin–like Growth Factor I Gene Expression by Growth Hormone", Proc. Natl. Acad. Sci. 83:9343–9347, 1986.
Quaife et al., "Histopathology Associated with Elevated Levels of Growth Hormone and Insulin–Like Growth Factor I in Transgenic Mice", Endocrinology 124:40–48, 1989.

*Primary Examiner*—Jasmine C. Chambers
*Assistant Examiner*—Jill D. Schmuck
*Attorney, Agent, or Firm*—William McGowan; Fish & Richardson; John D. Conway

[57] ABSTRACT

A transgenic mouse containing an IGF-1 transgene which is operably linked to a promoter sequence and is expressed in the pancreas of the mouse.

7 Claims, 2 Drawing Sheets

TRANSGENIC MOUSE CONTAINING AN IGF-1 TRANSGENE

CROSS REFERENCE TO RELATED APPLICATIONS

Under 35 USC § 120, this application claims the benefit of prior U.S. provisional application 60/004,260, filed Sep. 25, 1995.

BACKGROUND OF THE INVENTION

Diabetes mellitus is a serious metabolic disorder, with a world-wide incidence between 1 and 6 percent (Taylor, et al., Biochem. J. 250:625 (1988); McGarry, Science 258:766 (1992)). All forms of diabetes are characterized by hyperglycemia, a partial or total deficiency of insulin, zona glomerulosa of the kidney, and neurologic complications (Williamson, et al., Diabetes 42:801 (1993); Ruderman, et al., FASEB J. 6:2905 (1992); The Diabetes Control and Complications Trial Research Group, N. Engl. J. Med. 329:977 (1993)). Diabetes mellitus also results in the development of microvascular pathology in the retina and as a result is currently the leading cause of vision loss and blindness in adults.

Various models have been employed for the investigation of the biochemical basis of the development diabetic complications. These include experimentally induced insulin-dependent diabetes in animals treated with either streptozotocin (Tomlinson, et al., Pharmacol. Rev. 44:103 (1992); Portha, et al., Diabetes Metab. (Paris) 15:61 (1989)), or alloxan (Malaisse, et al., Proc. Natl. Acad. Sci. U.S.A. 79:927 (1982)), as well as various in vitro systems (Gillies, et al., Invest. Opthalmol. Vis. Sci. 34:3396 (1993); Grant, et al., Ann. NY Acad. Sci. 692:230 (1993)). In these chemically induced models, consistent diabetic complications have not been achieved (Frank, Diabetes 43:169 (1994)).

Various genetically defined animal models that spontaneously develop type I (Wicker, et al., Ann. Rev. Immunol. 13:179 (1995); Mordes, et al., Diabetes/Metab. Rev. 3:725 (1987); Guberski, et al., Diabetologia 36:912 (1993)) and type II diabetes (Shafrir, Diabetes/Metab Rev. 8:179 (1992)) have been described. Although analysis of the disease process in these animals have provided useful insights to the development of diabetes (Rossini, et al., Clin. Immunol. Immunopathol. 74:2 (1995)), none of these models develop microvascular pathology in either the eyes or kidneys. Therefore, there is a clear need for animal models of the disorder that closely mimic the pathophysiologic progression of both the disease and its complications in humans.

SUMMARY OF THE INVENTION

An aspect of this invention features a transgenic, non-human mammal (e.g., rodents such as mice or rats, dogs, cats, guinea pigs, rabbits, pigs, and sheep) containing an IGF-1 transgene which is operably linked to a promoter sequence and is expressed in the pancreas of the mammal. In certain instances, such a mammal develops diabetic complications (e.g., retinopathy, cataract, glaucoma, nephropathy, or microvascular changes). It was unexpected that a mammal containing an IGF-1 transgene expressed in the pancreas could be produced and would have the propensity to develop diabetes and its complications.

In one embodiment, the chromosome of the transgenic mammal includes an endogenous coding sequence the same or substantially the same as the coding sequence of the IGF-1 transgene (i.e., so that both sequences encode functional IGF-1 proteins), which is preferably integrated into a chromosome of the mammal at a site different from the location of the endogenous coding sequence. The IGF-1 transgene can also be the same or substantially the same as the IGF-1 gene of another species as long as it encodes a functional IGF-1 protein. Examples of an IGF-1 gene include, but are not limited to, mouse, rat, human, bovine, goat, pig, sheep, and guinea pig IGF-1 genes. Indeed, Non-mammalian IGF-1 genes from chicken, xenopus and salmon may also prove to be suitable. The transcription of the IGF-1 transgene is preferably under the control of a promoter sequence different from the promoter sequence controlling the transcription of the endogenous coding sequence. Examples of a promoter sequence effective for the expression of the IGF-1 gene in the pancreas of the mammal include an insulin gene-I promotor, an insulin gene-II promotor, an elastase gene-I promotor, an L-type pyruvate kinase gene promotor, and a glucagon genes promotor. The promoter may be inducible, e.g., insulin gene promoters which are induced by glucose.

In a mammal of the invention, the IGF-1 transgene may be contained in both the germ cells and somatic cells thereby allowing the mammal to be bred to produce progeny transgenic mammals; alternatively, the IGF-1 transgene may be contained only in the pancreatic cells.

Another aspect of the invention features a DNA fragment including an IGF-1 gene (e.g., human or mouse IGF-1 gene) and a promoter sequence, in which the promoter sequence is operably linked to the IGF-1 gene and is effective for the expression of the IGF-1 gene in pancreatic cells. The DNA fragment may be an integral part of a linear construct or of a vector (e.g., a plasmid or a viral vector).

In yet another aspect, the invention features a method of producing a transgenic, non-human mammal. The method includes the steps of: isolating a fertilized egg from a first female mammal (e.g., mouse); transferring a DNA fragment as described above into the fertilized egg; transferring the fertilized egg containing the DNA fragment to the uterus of a pseudo-pregnant, second female mammal; and maintaining the second female such that the second female mammal becomes pregnant with an embryo derived from the fertilized egg and the embryo develops into a transgenic, non-human mammal. The first female and the second female are preferably of the same species. Also, the transferred DNA fragment may be contained within a viral vector, a plasmid, or a linear construct.

In still another aspect, the invention features a second method of producing a transgenic, non-human mammal. The method includes the steps of: transforming embryonic stem cells with a DNA fragment described above under conditions wherein the DNA fragment becomes integrated into the chromosomes of the embryonic stem cells; selecting for embryonic stem cells containing the DNA fragment; introducing the selected cells into the blastocoel of a blastocyst of a mammal (e.g., mouse); and growing the blastocyst into the mammal. The embryonic stem cells preferably originate from the same species as the mammal. Also, the DNA fragment can be contained within a viral vector, plasmid (e.g., extrachromosomal plasmid), or linear construct; and can become integrated into a chromosome of an embryonic stem cell by homologous recombination or DNA-mediated transfection (e.g., electroporation).

In a further aspect, the invention features a third method of producing a transgenic, non-human mammal. The method includes the step of introducing a DNA fragment as described above directly into the pancreas of the mammal. The DNA fragment to be introduced may be an integral part of a viral vector, a plasmid, or a linear construct.

The present invention also features a method of evaluating the effect of a therapeutic agent to treat diabetes. The method includes the steps of: administering the agent to a transgenic, non-human mammal as described above; and evaluating the effect of the agent on glucose tolerance or diabetic complications of the mammal. Examples of diabetic complications include the development of cataract or retinopathy (in the eye), nephropathy (in the kidney), neuropathy, and microvascular disease. The effect of the agent (e.g., delaying or stimulating) of the onset of diabetes or diabetic complications can be measured against a control standard. For example, the effect of the agent on glucose tolerance of the mammal can be evaluated by administering glucose to the mammal and measuring the ability of the mammal to remove the glucose from its blood (e.g., uptake by muscle cells). Furthermore, the effect of the agent on the onset of diabetic complications can also be ascertained by determining the time at which the mammal obtains ocular or kidney complications. These tests are sensitive because of the propensity of the mammal to develop diabetes and diabetic complications.

Also contemplated within this invention are cells, tissues, and organs derived from a transgenic mammal of the invention, or cultured cells into which a DNA fragment described above has been introduced. Cells, tissues, and organs derived from the transgenic mammals can be used to conduct in vitro cell, tissue, and organ culture assay to evaluate the effect of a therapeutic agent to treat diabetes and its complications. Examples of such cells include pancreatic cells (e.g., alpha, beta, delta, and pancreatic polypeptide containing (PP) cells), as well as ocular cells (e.g., retina cells), muscle cells, and liver cells. Examples of such tissues and organs include muscle, liver, pancreas, retina, microvessels, and eye lens.

Also included within the scope of this invention is a method of evaluating a therapeutic agent to treat diabetes or diabetic complications. The method includes the steps of: contacting the agent with the just-described cells; and evaluating the pharmaceutical effect of the agent on the cell (insulin secretion of a pancreatic cell; or glucose metabolism of a muscle cell or a liver cell).

Other features and advantages of the present invention will be apparent from the brief description of the drawings, detailed description, and from the claims.

BRIEF DESCRIPTION OF THE DRAWING

The drawings are first briefly described.

DETAILED DESCRIPTION OF THE INVENTION

Figure 1:
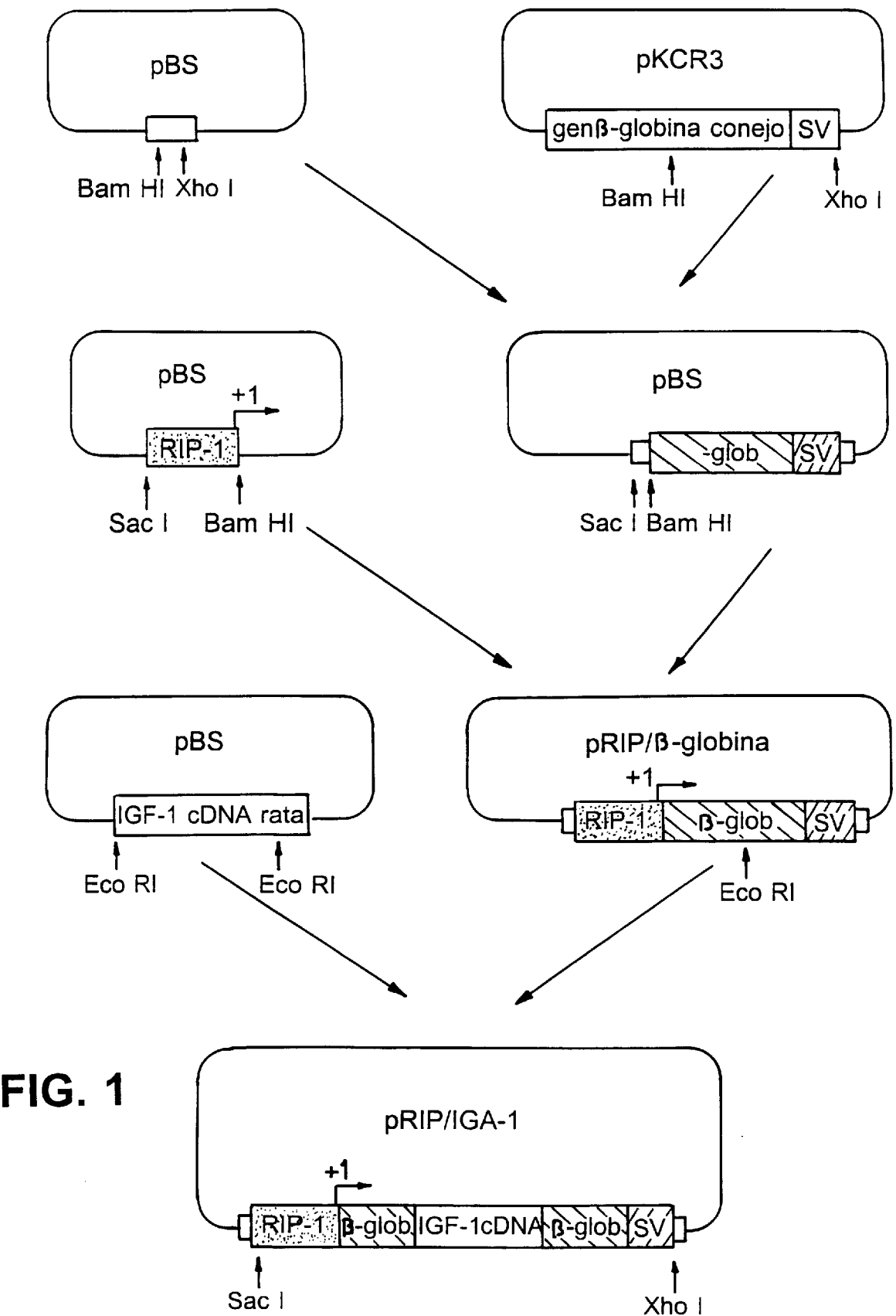
FIG. 1 is a diagrammatic representation of the construction of a DNA vector containing an IGF-1 gene.

The methods of making and using the transgenic, non-human mammals of this invention are well within the ability of a person of ordinary skill in the art. Unless defined otherwise, all technical and scientific terms used herein have the same meaning as commonly understood by one of ordinary skill in the art to which this invention belongs. Also, all publications mentioned herein are incorporated by reference.

The transgenic, non-human mammal of the invention overexpresses (e.g., at a higher level than naturally-occurring mammals) IGF-1 in the cells of the pancreas. The overexpression of IGF-1 in the microenvironment of the pancreas results in a reduced response of the pancreas to high physiological levels of glucose (e.g., to a meal or glucose challenge) with a consequent reduced production of insulin to effect glucose homeostasis. The consequence is a genetically modified mammal that exhibits impaired glucose tolerance in a manner similar to the late prediabetic stage in the development of diabetes mellitus in humans (National Diabetes Data Group, Diabetes 28: 1039 (1979); World Health Organization, Diabetes mellitus: A report of a WHO study group, Technical Report Series, 727, WHO, Geneva (1985)). Distinct from the previous systems described above in the Background of the Invention, the circulatory concentration of IGF-1 in the mammals of the invention remain normal, which allows the precise assessment of the paracrine effect of the hormone on pancreatic (e.g., β-cell) function in the pathogenesis of impaired glucose tolerance.

The mammals of the invention also have a propensity to spontaneously develop microvascular alterations manifesting in ocular histopathology. Lens opacities and cataracts occur at 4–10% of juvenile diabetics (L'Esperance, et al, In: Diabetes Mellitus-Theory and Practice, Third Ed., Ellenberg, et al. (eds), Medical Examination Publishing Co., 727–757 (1983)) and may result from sorbital accumulation within the lens (Kador, Exp. Eye Res., 50:615 (1990)). The ocular complication of the mammals of the invention develop not as direct alteration in circulating or local concentrations of IGF-1 levels in the eyes, but indirectly in response to an altered regulation in pancreatic physiology, a situation that is more akin to clinical diabetes.

What is meant by "transgene" herein is any exogenous gene sequence which is introduced into both the somatic and germ cells or only some of the somatic cells of a mammal. The transgene may or may not be an integral part of a chromosome. If the transgene is integrated into a chromosome, it may or may not be located at the same site as its corresponding endogenous gene sequence. The transgene of the invention includes an IGF-1 gene or its complementary DNA (cDNA), whose expression in the pancreas (e.g., the β-cells of the islet of Langerhans) is driven by a tissue specific promoter. The expression of the transgene may be precisely regulated (e.g., inducible) by changes in the circulating glucose levels or by hormones (Docherty, et al., FASEB J. 8:20 (1994)).

The DNA sequences of the IGF-1 cDNA and the IGF-1 gene for various species have been reported. Examples include bovine (Fotsis, et al., Nucleic Acid Res. 18:676 (1990)), goat (Yoshikawa, et al., GenBank Accession # GOTIGFI), pig (Tavakkol, et al., Mol. Endocrinol. 2:674 (1988)), sheep (Wong, et al., DNA 8:649 (1989)), human (Dull, et al., Nature 310:777 (1984); de Pagter-Holthuizen, et al., FEBS Lett. 195:179 (1986)), rat (Roberts, et al., Mol. Endocrinol. 1:243 (1987); Shimatsu, et al., J. Biol. Chem. 262:7894 (1987)), guinea pig (Bell, et al., Nucleic Acid Res. 18:4275 (1990)), chicken (Kajimoto, et al., Mol. Endocrinol. 3:1907 (1989)), xenopus (Kajimoto, et al., Mol. Endocrinol. 4:217 (1990)), and salmon (Cao, et al., Mol. Endocrinol. 3:2005 (1989)).

Histologically, the pancreas is composed of exocrine and endocrine glands. The exocrine component constitutes 80–85 percent of the organ and is made up of numerous acini. The endocrine component (e.g., islet of Langerhans) is made up of four main cell types: α-, β-, δ- and pancreatic polypeptide containing (PP) cells (Robbins Pathologic Basis of Disease, Cotran, et al. (eds), 4th Ed., W. B. Saunders Co. (1989)).

The promoter is comprised of cis-acting DNA sequences which is capable of directing the transcription of a gene in the appropriate tissue environment and in response to physiological regulators. Preferably the promoter used is the insulin gene promoter. The insulin genes (I & II) are exclusively expressed in the pancreatic β-cells of the islets of Langerhans (Hanahan, Nature 315:115 (1985); Philippe, Endocrine Rev. 12:252 (1991)). These promoters have previously been used to direct the expression of a large number of exogenous genes in β-cells of transgenic animals including oncogenes (Tal, et al., Proc. Natl. Acad. Sci. U.S.A. 89:5744 (1992); Efrat, et al., Proc. Natl. Acad. Sci. U.S.A. 85:9037 (1988)), genes involved in the immunomodulation (Sarvetnick, et al. Nature 346:844 (1990); Bohme, et al., Science 244:1179 (1989); Stewart, et al., Science 260:1943 (1993)), genes encoding enzymes that control key metabolic points (Epstein, et al., Proc. Natl. Acad. Sci. U.S.A. 89:12038 (1992); Efrat, Proc. Natl. Acad. Sci. U.S.A. 91:2051 (1994)), nerve growth factors (Edwards, et al., Cell 58:161 (1989)), and viral genomes (Oldstone, et al., Cell 65:319 (1991)).

A number of other promoters are also known to direct the expression of exogenous genes to specific cell-types in the pancreas. These include, the elastase-I gene promoter, which directs expression to the acinar cells (Ornitz, et al., Science 238:188 (1987)), the L-type pyruvate kinase gene promoter which directs expression to islet cells (Cartier, et al., Oncogene 7:1413 (1992)), and the glucagon gene promoter which directs expression to the α-cells (Efrat, et al., Neuron 1:605 (1988); Philippe, J., Endocrine Rev. 12:252 (1991)).

A number of methods have been used to obtain transgenic, non-human mammals. By transgenic non-human mammals is meant a mammal that has gained an additional gene from the introduction of an exogenous gene sequence, i.e., transgene, into its own cells (e.g., both the somatic and germ cells, or just the pancreatic cells), or into an ancestor's germ line.

There are a number of methods to introduce the exogenous DNA into the germ line (e.g., introduction into the germ or somatic cells) of the mammal. One method is by microinjection of the gene construct into the pronucleus of an early stage embryo (e.g., before the four-cell stage) (Wagner, et al., Proc. Natl. Acad. Sci. U.S.A. 78:5016 (1981); Brinster, et al., Proc Natl Acad Sci U.S.A. 82:4438 (1985)). The detailed procedure to produce such transgenic mice has been described (see e.g., Hogan, et al., Manipulating the Mouse Embryo, Cold Spring Harbour Laboratory, Cold Spring Harbour, N.Y. (1986); U.S. Pat. No. 5,175,383 (1992)). This procedure has also been adapted for other mammalian species (e.g., Hammer, et al., Nature 315:680 (1985); Murray, et al., Reprod. Fert. Devl. 1:147 (1989); Pursel, et al., Vet. Immunol. Histopath. 17:303 (1987); Rexroad, et al., J. Reprod. Fert. 41 (suppl):119 (1990); Rexroad, et al., Molec. Reprod. Devl. 1:164 (1989); Simons, et al., BioTechnology 6:179 (1988); Vize, et al., J. Cell. Sci. 90:295 (1988); and Wagner, J. Cell. Biochem. 13B (suppl) :164 (1989)).

Another method for producing germ-line transgenic mammals is through the use of embryonic stem cells. The gene construct may be introduced into embryonic stem cells by homologous recombination (Thomas, et al., Cell 51:503 (1987); Capecchi, Science 244:1288 (1989); Joyner, et al., Nature 338: 153 (1989)) in a transcriptionally active region of the genome. A suitable construct may also be introduced into the embryonic stem cells by DNA-mediated transfection, such as electroporation (Ausubel, et al., Current Protocols in Molecular Biology, John Wiley & Sons (1987)). Detailed procedures for culturing embryonic stem cells (e.g. ES-D3, ATCC# CCL-1934, ES-E14TG2a, ATCC# CCL-1821, American Type Culture Collection, Rockville, Md.) and the methods of making transgenic mammals from embryonic stem cells cab be found in Teratocarcinomas and Embryonic Stem Cells, A practical Approach, ed. E. J. Robertson (IRL Press, 1987).

In the above methods for the generation of a germ-line transgenic mammals, the construct may be introduced as a linear construct, as a circular plasmid, or as a viral vector which may be incorporated and inherited as a transgene integrated into the host genome. The transgene may also be constructed so as to permit it to be inherited as an extrachromosomal plasmid (Gassmann, M. et al., Proc. Natl. Acad. Sci. U.S.A. 92:1292 (1995)). The term plasmid is meant to describe a DNA molecule that can replicate autonomously in a host such as a bacterium or yeast.

The transgenic, non-human mammal of this invention may also be obtained by infection of cells of the pancreas either in vivo (e.g., direct injection) or ex vivo (e.g., infecting the cells outside the host and later reimplanting) or in vitro (e.g. infecting the cells and reimplanting into syngenic hosts) with a recombinant viral vector carrying an IGF-1 gene. Examples of suitable viral vectors include recombinant retroviral vectors (Valerio, et al., Gene 84:419 (1989); Scharfman, et al., Proc. Natl Acad. Sci. U.S.A. 88:462 (1991); Miller, D. G. & Buttimore, C., Mol. Cell. Biol. 6:2895 (1986)), recombinant adenoviral vectors (Freidman, et al., Mol. Cell. Biol. 6:3791 (1986); Levrero, et al., Gene 101:195 (1991)), and recombinant Herpes simplex viral vectors (Fink, et al., Human Gene Therapy 3:11 (1992)). Recombinant retroviral vectors capable of transducing and expressing structural genes (e.g., IGF-1 coding genes) inserted in its genome are produced by transfecting the recombinant retroviral genome in suitable packaging cell lines such as PA317 and Psi-CRIP (Cornette, et al., Human Gene Therapy 2:5 (1991); Cone et al., Proc. Natl. Acad. Sci. U.S.A. 81:6349 (1984)). This approach offers a wide range of host and tissue tropism. Recombinant adenoviral vectors infect a wide variety of cells and tissue in susceptible hosts (e.g., cotton rat, hamster, dog, and chimpanzee) (Hsu, et al., J. Infectious Disease 166:769 (1992)), and also have the distinct advantage of not requiring mitotically active cells for infection.

The transgenic, non-human mammals of this invention can be used to screen for therapeutic agents for treating diabetes. More specifically, ocular abnormalities, cataracts, glaucoma and retinopathy are present in patients with type I and type II diabetes mellitus. The transgenic, non-human mammals of this invention reproducibly develop the metabolic disorder of glucose homeostasis, as evidenced by impaired glucose tolerance, as well as ocular complications. Such mammals thus provide a valuable system for the evaluation of the mechanisms underlying the development of diabetes as a result of altered insulin secretion and the biochemical/endocrine relationship to the onset and progression of diabetic complications. These mammals also offer a useful in vivo model for the assessment of the efficacy of emerging therapies for diabetes and its associated complications.

For example, an agent (e.g., an insulin agonist) is administered to a transgenic, non-human mammal of the invention. The ability of the agent to restore normal glucose disposal from the blood stream or the mammal's subsequent response to an intraperitoneal injection of glucose is examined. This response can be compared with the response of another mammal of this invention that has not received the agent, and with the response of a non-transgenic mammal that also has not received any treatment. The return of blood glucose concentration to pretreatment levels within a time period (e.g., 180 min) is an indication of efficacy of the agent.

A mammal of the invention can also be treated with an agent (e.g., an adolase reductase inhibitor (McCaled, et al., Diabetologia 34:695 (1991)), an aminoguanidine (Hammes, et al., Proc. Natl. Acad. Sci. U.S.A. 88:11555 (1991), or an angiotensin-converting enzyme inhibitor (Capek, et al., Clin. Invest. 72:961 (1994)) in parallel with another mammal of this invention that has not received the treatment. The comparative lowering of diabetic complications such as the incidence of cataracts or retinopathy, development of glomerulonephropathy, or the delay in the onset of these pathologic outcomes in the treated mammal is an indication of efficacy of the agent. Procedures for fundus photography and fluorescein angiography typically used to assess ocular changes has been developed for small laboratory animal eyes (Diloreto Jr., et al., Current Eye Research 13:157 (1994)). Other methods and intermediate endpoints for determining the effect of treatment have previously been described (Robinson, Jr., et al., Exp. Eye Res. 50:355 (1990); Hammes, et al., Proc. Natl. Acad. Sci. U.S.A., 88:11555 (1991); Hammes, et al., Diabetologia 38:269 (1995); Hammes, et al., Diabetologia 34:695 (1991); Kern, et al., Invest. Ophthalmol. Vis. Sci. 36:490 (1995); Remuzzi, et al., Kidney Int. 47:1319 (1995); and Sawicki, et al., Eur. J. Clin. Invest. 24:651 (1994)).

The transgenic, non-human mammals of this invention can also be used as a source of cells, tissues, or organs for cultures. Cells, tissues, and organs are cultured using standard tissue culture techniques (e.g., A Dissection and Tissue Culture Manual of the Nervous System, Shahar, et al. (eds), Alan R. Liss Inc. (1989); Animal Cell Culture, Pollard, et al. (eds), Humana Press (1989)). The in vitro function of these cells and tissues (e.g., muscle, liver, kidney, pancreatic, and eye cells), in the presence and absence of test agents, can be evaluated in a variety of assays to determine the activity of the test agents.

For example, the preparation of a hind limb muscle for perfusion studies to examine the uptake of glucose by the skeletal muscle has previously been described (Klip, et al., FEBS Lett., 224:224 (1987)). The assessment of carbohydrate metabolism from isolated strips of skeletal muscle in an in vitro assay has also been described (Leighton, et al., Biochem. J. 269:19 (1990); Chandry, et al., Biochimica Biophysica Acta, 177:527 (1969)). In another example, preparations of perfused isolated liver for the assessment of glycogen metabolism are described in Methods in Diabetes Research, Vol. 1, Laboratory Methods, part B, Larner, et al. (eds), John Wiley & Sons, 143–151 (1984). Similar analysis may be conducted in hepatocytes prepared from transgenic, non-human animal livers (Massague, et al., Am. J. Physiol. 257(1 Pt 1):E74 (1989)).

The pancreas from the transgenic, non-human mammals of the invention may also be isolated for perfusion studies to examine the regulation of insulin secretion (Dunmore, et al., J. Endocrinol., 137:375 (1993)). The islet of Langerhans can be isolated (Lacy, et al., Diabetes 16:35 (1967); Lernmark, et al., J. Cell. Biol. 71:606 (1976)) and cultured for perfusion studies for the assessment of the effects of agents capable of regulating islet cell secretion and autocrine/paracrine activities (Petterson, et al., Acta Physiol. Scand., 138:389 (1990)).

The retinal capillary pericytes and retinal endothelial cells can also be isolated and cultured for the assessment of agents that could affect the growth and biological responses of these cells in vitro (Wong, et al., Invest. Ophthalmol Vis. Sci. 28:1767 (1987); Gitlin, et al., Microvasc. Res. 26:74 (1983); Grant, et al., Ann. N.Y. Acad. Sci. 692:230 (1993); Grant, et al., Invest. Ophthalmol. Vis. Sci. 32:53 (1991)).

The following are examples of the method of making and using a transgenic, non-human mammal expressing an IGF-1 transgene in its pancreas. It is believed that one skilled in the art can, based on the description herein, utilize the present invention to its fullest extent. The specific embodiments set forth below are, therefore, to be construed as merely illustrative, and not limitative of the remainder of the disclosure in any way whatsoever.

Construction of a fusion rat insulin gene-I promoter/mouse IGF-1 gene construct

Restriction endonucleases and the other enzymes used for recombinant DNA manipulation were obtained from conventional commercial sources such as New England Biolabs (Beverly, Mass.), Promega Biological Research Products (Madison, Wis.) and Stratagene (LaJolla, Calif.). Radioactive material were obtained from conventional commercial sources such as New England Nuclear (Boston, Mass.) and Amersham Life Sciences (Arlington Heights, Ill.). Recombinant DNA manipulations were conducted using standard techniques known in the molecular biology art (e.g., Maniatis, et al., Molecular Cloning: A Laboratory Manual, CSHL (1982)).

As depicted in FIG. 1, the rat insulin gene-I promoter (RIP-I) was isolated as a 573 bp SacI-BamHI fragment (−570 to +3) from the plasmid pRIP-I-Tag (Hanahan, Nature 315:115 (1985); Dandoy-Dron, et al., N. Acid. Res. 19:4925 (1991)). A BamHI-XhoI fragment comprising of the last two exons and the last intron rabbit β-globin gene (genβ-globina conejo) linked to the 3'-region of the SV40 (SV) enhancer was isolated from the plasmid pKCR3 (Landais, et al., J. Immunol. 137:3002 (1986)). This segment, which provides both the splice donor and acceptor sites (β-glob) and a polyadenylation site, was subcloned into the BamHI and XhoI sites of the plasmid pBS (Bluescript, Stratagene, LaJolla, Calif.). The expression vector pRIP/β-globina was generated by ligating the 573 bp SacI-BamHI fragment of rat insulin gene-I promoter into the SacI and BamHI cloning sites of the pBS-β-globin construct above.

The mouse IGF-1 cDNA (Bell, G. I., et al., Nucleic acid Res. 14:7873 (1986)) was employed as the structural gene. The mouse IGF-1 cDNA was isolated as a 720 bp EcoRI fragment containing the entire coding sequence of the preprohormone, including 5' and 3' untranslated region (Bell, et al., Nucleic acid Res. 14:7873 (1986)) from the plasmid pmigf1-2 (PBS-IGF-1 cDNA rata) (ATCC# 63070, American Type Culture Collection, Rockville, Md.). The IGF-1 gene construct (pRIP/IGF-1) was assembled by inserting the 720 bp EcoRI fragment of the mouse IGF-1 into the unique EcoRI site with the β-globin sequence.

Construction of transgenic mice

DNA for microinjection was prepared by cleaving the pRIP/IGF-1 construct with the restriction enzymes SacI and XhoI. The cleaved DNA was fractionated by electrophoresing on a 0.7% Agarose gel in TBE buffer (Maniatis, T., et al., Molecular Cloning: A Laboratory Manual, CSHL (1982)). A band containing the 3.4 kb SacI-XhoI fragment comprising of the IGF-1 gene was visualized by ethidium bromide staining, excised, and the DNA recovered by electroelution. The DNA was extracted with phenol-chloroform (1:1), precipitated in ethanol, redissolved in a low salt buffer (0.2M NaCl, 20 mM Tris, pH 7.4 and 1 mM EDTA (Reagents obtained from Sigma, St. Louis, Mo.)), and purified on Elutip-D™ columns (Schleicher & Schuell Inc., Keene, N.H.) according to vendor's instructions.

For microinjection, DNA concentration was adjusted to 2 ug/ml in 5 mM Tris, pH 7.4, and 1 mM EDTA. Fertilized mouse eggs were harvested by flushing the oviduct of superovulated C57BL56/SJL mice 6–8 hr after mating. The male pronuclei of the zygotes were injected with 2 pl of the DNA solution as previously described (Wagner, et al., Proc. Natl. Acad. Sci. U.S.A. 78:5016 (1981)). Viable embryos were then reimplanted into pseudopregnant females (Hogan, B., et al., Manipulating the Mouse Embryo, CSHL (1986)) for the production of transgenic mice.

For the identification of transgenic founder mammals ($F_o$), tail samples (1–2 cm) were removed from three week old mice. The DNAs from the tails were prepared and analysed by both southern blotting using probes complementary to the IGF-1 gene, and by polymerase chain reaction (PCR) using suitable PCR primers to the IGF-1 gene. Transgenic mammal lines were established and bred as previously described (Hogan, et al., Manipulating the Mouse Embryo, CSHL (1986)).

A southern blot analysis of EcoRI-digested genomic DNA from control and two transgenic mouse lines were performed with a $^{32}$P-labelled mouse IGF-1 cDNA as the probe. Two hybridizing fragments were apparent on the blot, a 2.2 kb fragment and a 0.72 kb fragment. The 2.2 kb fragment corresponded to the endogenous mouse IGF-1 gene and was present in both the control and transgenic lines. The 0.72 kb fragment was derived from the transgene and was present in high copy number (50 copies) with respect to the endogenous gene.

Expression of the IGF-1 transgene

Because not every mammal will express the transgene, it is necessary to characterized each mammal line with respect to expression (mRNA and protein) in different tissues. Northern blot analysis with a $^{32}$P-labelled IGF-1 cDNA probe and reverse transcriptase-PCR (RT-PCR) analysis of total RNA, prepared from various tissues of transgenic and control mice were conducted.

In a northern blot analysis of total RNA from pancreas of a control and a transgenic mouse, a 0.8 kb mRNA transcript corresponding to the expression of the endogenous IGF-1 message was detected in both the control and transgenic pancreases. A 1.2 kb mRNA transcript corresponding to the message transcribed off the IGF-1 transgene was detected only in the transgenic pancreas. The high level of overexpression of the transgene in the tissue was evidenced by the intensity of the band relative to the endogenous transcript.

The overexpression of IGF-1 was also evident in the western blot analysis of total cellular lysate of islets prepared from control and transgenic pancreas. The amount of IGF-1 produced was detected on immunoblot using a rabbit antiserum to IGF-1 (GroPep, Adelaide, Australia). This confirmed that the level of IGF-1 produced by islets of the transgenic mammal was significantly higher than that in the control mammal.

RT-PCR analysis of total RNA prepared from a pancreatic islets, liver, kidney and eye of control and transgenic mice indicated that a PCR-amplified DNA band corresponding in size to the positive control band was detected only in RNA isolated from the pancreas of the IGF-1 transgenic mammal. The data supports the selective expression of the IGF-1 transgene in pancreatic tissues. No transgene expression was detected in the liver, kidney, and eye of the IGF-1 transgenic mice.

IGF-1 and the pathogenesis of diabetes

In isolated islet assays, it has been previously demonstrated that IGF-1 at physiological concentrations will inhibit glucose-stimulated insulin secretion (Leahy, et al., Endocrinology 126:1593 (1990)). IGF-1 infusion in man and animals also results in a reduction in plasma insulin (de Zegher, et al., Endocrinology 123:658 (1988); Guler, et al., Proc. Natl. Acad. Sci. U.S.A. 86:2868 (1989); Jacobs, et al., J. Clin. Invest. 83:1717 (1989)). Thus, the influence of overexpression of IGF-1 in the pancreas in the transgenic mice on glucose homeostasis was examined, noting that the transcriptional activity of insulin gene-I promoter used in the construction of the transgenic mice is glucose inducible. The results of the study are shown in Table 1.

TABLE 1

| | Diet | | | |
| --- | --- | --- | --- | --- |
| | Standard Diet | | High CHO Diet | |
| Assay | Con | Tg | Con | Tg |
| Glucose (mg/dL) | 148 ± 7 | 205 ± 10 | 157 ± 15 | 248 ± 21 |
| Insulin (ng/mL) | 1.4 ± 0.1 | 3.1 ± 0.2 | 2.9 ± 0.4 | 1.5 ± 0.2 |
| IGF-1 (ng/mL) | 231 ± 34 | 170 ± 25 | 135 ± 21 | 97 ± 15 |

On a normal diet, the transgenic mice ("Tg") were mildly hyperglycemic compared to control mice ("Con"). There was no evidence of increase in plasma levels of IGF-1. Hyperglycemia could account for the observed higher plasma insulin levels in the basal state. On a diet high in carbohydrates ("CHO") (Valera, et al., J. Biol. Chem. 269:28543 (1994); Nutritional Biochemical Corp., Cleveland, Ohio), which resulted in the induction of the transgene expression, there was a compensatory suppression of insulin secretion in the transgenic mice. The resulting induction in transgene expression, however, did not increase circulating levels of IGF-1, indicating that the effect of the hormone on insulin secretion from the β-cells was autocrine/paracrine. This observation supports the possibility that overexpression of IGF-1 in adjacent cells (for example, α- and δ-cells) of the islets/pancreas will also produce a similar suppression of insulin secretion. The transgenic mice fed the high carbohydrate diet for two weeks also exhibited a further elevation of steady state plasma glucose level consistent with the development of diabetes.

Figure 2A:
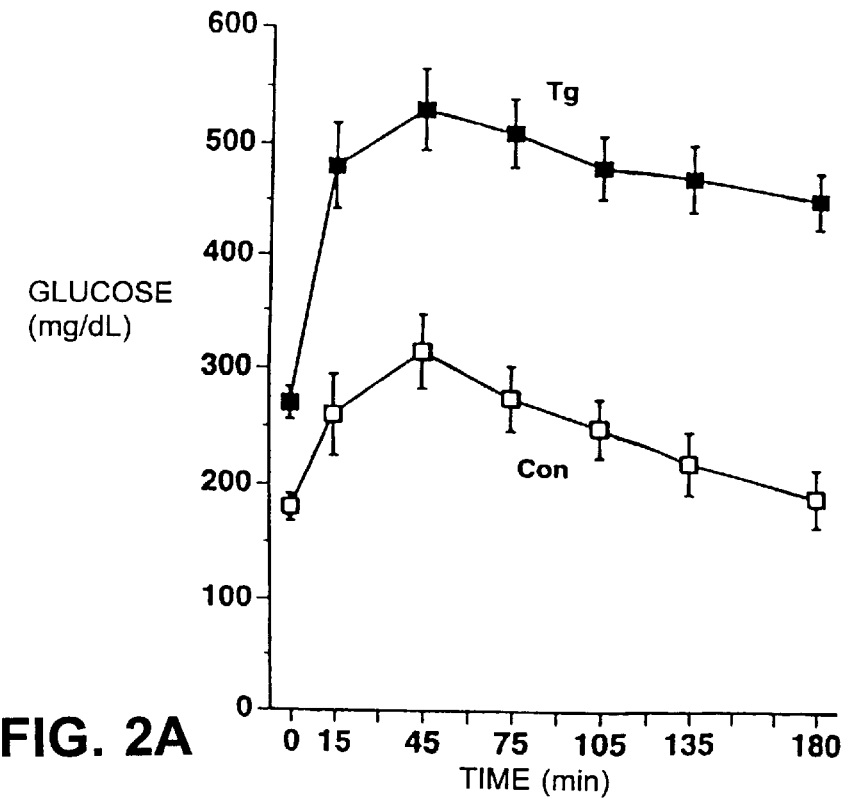
FIG. 2A is a plasma glucose profile after an intraperitoneal glucose challenge (1 mg of glucose/g of body weight in transgenic mice ("Tg;" filled boxes) and control mice ("Con;" open boxes).

Impaired glucose tolerance was also evident in transgenic mice fed a high carbohydrate diet. As indicated in FIG. 2A, administration of an intraperitoneal glucose tolerance test (Valera, et al., J. Biol. Chem. 269:28543 (1994)) demonstrated that in the control mice, plasma glucose levels return to basal values after 180 min, while plasma glucose levels remained significantly elevated in the transgenic mice over the same time period.

Figure 2B:
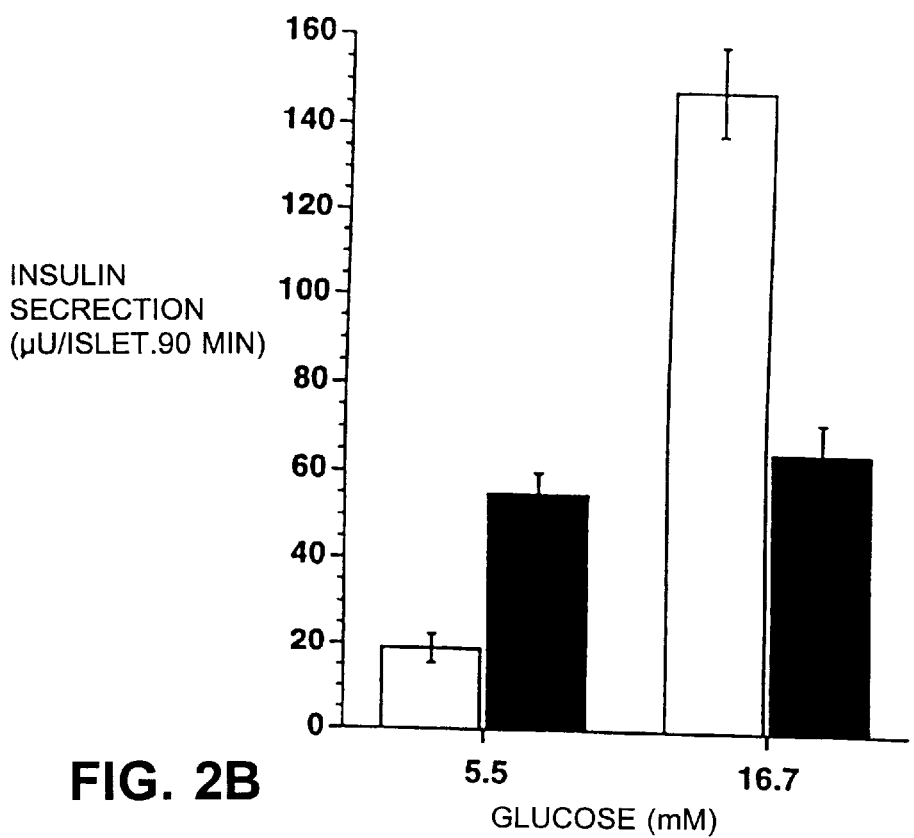
FIG. 2B is a graph showing glucose-induced insulin secretion from isolated islets prepared from control mice (open bars) and transgenic mice (filled bars).

Further analysis of the regulation of in vitro insulin secretion in islets isolated from fed transgenic and fed control mice (FIG. 2B) indicated that although insulin secretory potential was higher in transgenic mouse islets compared to control at basal (5 mM) glucose concentration, insulin secretion was not substantially induced at high glucose concentration (16.7 mM) in the former compared to control islets. Since the IGF-1 transgene expression is induced at high glucose, this result suggests that an inhibition of insulin secretion by the transgene is the likely mechanism for the refractoriness of the transgenic islets to glucose stimulation, which confirms the in vivo observations described above.

Effect of IGF-1 transgene expression on the development of diabetic complications Ocular complications were also observed in all of the transgenic mice expressing the RIP/IGF-1 transgene. Female animals, after a few pregnancies, presented complications earlier than males. At 6 months old, mature bilateral cataracts developed in female animals with complete lens opacities. Incipient cataracts were detected by slit-lamp biomicroscopy (see Robbins Pathologic Basis of Disease, Cotran, et al. (eds), 4th Ed., W. B. Saunders Co. (1989)) as early as 2 months of age in the female and about 4 months in the male transgenic mice. The ocular complications ranged from superficial posterior cortex involvement (e.g., cortical cataract) at early stages, to complete lens opacities (e.g., mature cataract). Superficial corneal blood vessels and keratopathy, characterized by recurrent epithelial erosion, were also present on most eyes. Bilateral defects in the iris and the anterior chamber angle were also observed. These include iris neovascularization, hyphema, and adhesions between the iris and cornea (peripheral anterior synechia) and between the iris and lens (posterior synechia). Glaucoma was also present in the eyes of the transgenic mice.

Other Embodiments

It is to be understood that while the invention has been described in conjunction with the detailed description thereof, that the forgoing description is intended to illustrate and not limit the scope of the invention, which is defined by the scope of the appended claims. Other aspects, advantages, and modifications are within the claims.

What is claimed is:

1. A transgenic mouse whose germ cells and somatic cells comprise an insulin growth factor-1 (IGF-1) transgene comprising DNA encoding IGF-1 operably linked to a promoter sequence effective for expression of IGF-1 in the pancreas of said mouse, wherein with respect to the corresponding wild-type mouse, expression of said IGF-1 results in said transgenic mouse exhibiting no elevated level of circulating IGF-1, a greater than 5-fold level of IGF-1 mRNA expression in the pancreas, and at least one diabetic complication selected from the group consisting of increased plasma glucose levels upon glucose inducibility, retinopathy, cataracts, glaucoma, and microvascular changes in the eye of said mouse.

2. The transgenic mouse of claim 1, wherein said transgene comprises DNA encoding mouse IGF-1.

3. The transgenic mouse of claim 1, wherein said promoter sequence is selected from the group consisting of an insulin gene-I promoter and an insulin gene-II promoter.

4. The transgenic mouse of claim 1, wherein said transgene comprises DNA encoding human IGF-1.

5. A method of evaluating a therapeutic agent to treat diabetes or diabetic complications, said method comprising:

administering said agent to a mouse according to claim 1 and evaluating the pharmaceutical effect of said agent on said mouse.

6. A method according to claim 5, wherein said agent is administered directly to an eye or eyes of said mouse and wherein said pharmaceutical effect of said agent on said eye or eyes of said mouse is evaluated.

7. A method according to claim 6, wherein said agent is administered or contacted with cells of the eye or eyes of said mouse and wherein said pharmaceutical effect of said agent on said cells of the eye or eyes of said mouse is evaluated.

* * * * *